United States Patent
Chiba et al.

(10) Patent No.: US 10,519,507 B2
(45) Date of Patent: Dec. 31, 2019

(54) METHOD FOR DETECTING T-CELL LYMPHOMA

(71) Applicant: University of Tsukuba, Tsukuba-Shi (JP)

(72) Inventors: Shigeru Chiba, Ibaraki (JP); Mamiko Yanagimoto, Ibaraki (JP); Seishi Ogawa, Tokyo (JP)

(73) Assignee: University of Tsukuba, Tennodai, Tsukuba-shi, Ibaraki (JP)

( * ) Notice: Subject to any disclaimer, the term of this patent is extended or adjusted under 35 U.S.C. 154(b) by 338 days.

(21) Appl. No.: 14/888,206

(22) PCT Filed: May 1, 2014

(86) PCT No.: PCT/JP2014/062112
§ 371 (c)(1),
(2) Date: Oct. 30, 2015

(87) PCT Pub. No.: WO2014/178432
PCT Pub. Date: Nov. 6, 2014

(65) Prior Publication Data
US 2016/0076107 A1   Mar. 17, 2016

(30) Foreign Application Priority Data

May 1, 2013   (JP) .................. 2013-096582

(51) Int. Cl.
*C12Q 1/6886* (2018.01)
(52) U.S. Cl.
CPC ..... *C12Q 1/6886* (2013.01); *C12Q 2600/156* (2013.01); *C12Q 2600/158* (2013.01)
(58) Field of Classification Search
None
See application file for complete search history.

(56) References Cited

PUBLICATIONS

Rihet (J Cancer Res Clin Oncol, Dec. 2001, 127(12): 733-8).*
Manso et al. (Blood, May 2014, vol. 123, No. 18, p. 2893-2894).*
Ionnidis (Plost Med, 2005, 2(8):e124, p. 696-701).*
Hegele, Arterioscler. Thromb. Vasc. Biol, 2002, 22: 1058-1061.*
Juppner, Bone, Aug. 1995, vol. 17, No. 2, pp. 39S-42S.*
International Search Report for PCT/JP/2014/062112 dated Jul. 2, 2013 with English translation.
De Leval L. et al, Blood, 2007, vol. 109, No. 11, p. 4952-4963, entire text.
Lemonnier F. et al, Blood, 2012, vol. 120, No. 7, p. 1466-1469, entire text.
Couronne L. et al, N. Engl. J. Med., 2012, vol. 366, No. 1, p. 95-96, entire text.
*Homo sapiens* GTP-binding protein (rhoA) mRNA, complete cds. [online]. Aug. 2, 1999 uploaded. NCBI Entrez Nucleotide, Accession No. L25080 (GI:407696) [Retrieved on May 27, 2014]. Retrieved from the internet: <URL: http://www.ncbi.nlm.nih.gov/nuccore/L25080>, entire text.
Sakata-Y. M. et al, Nat. Genet., Feb. 2014, vol. 46, No. 2, 171-175, entire text.
J. Clin. Oncol. Jan. 10, 2013; 31(2):240-6.

* cited by examiner

*Primary Examiner* — Sarae L Bausch
(74) *Attorney, Agent, or Firm* — Mintz Levin Cohn Ferris Glovsky and Popeo, P.C.

(57) ABSTRACT

A method for detecting T-cell lymphoma characterized in that gene mutations of at least one base selected from a group comprising base numbers 50, 331, 334, and 482 or gene mutations of base numbers 49 to 51 in the base sequence of an RHOA gene collected from a subject are analyzed, and the analysis results and T-cell lymphoma are associated with each other.

1 Claim, 7 Drawing Sheets

Specification includes a Sequence Listing.

METHOD FOR DETECTING T-CELL LYMPHOMA

RELATED APPLICATIONS

This application is a national stage application, filed under 35 U.S.C. § 371, of International Application No. PCT/JP2014/062112, filed on May 1, 2014, which claims the benefit of and priority to Japanese Application No. 2013-096582, filed May 1, 2013, the contents of which are incorporated herein by reference in their entireties.

SEQUENCE LISTING

The contents of the text file named "49807_501N01US_Sequence_Text.txt," which was created on Oct. 29, 2015 and is 6 KB in size, are hereby incorporated by reference in their entirety.

TECHNICAL FIELD

The present invention relates to a method for detecting a T-cell lymphoma using a mutation in RHOA gene as an indicator.

BACKGROUND ART

Angioimmunoblastic T-cell lymphoma (AITL) is one form of peripheral T-cell lymphoma (PTCL), and a disease that accounts for about 20% of the entire T-cell lymphomas. AITL often presents autoimmune-disorder-like clinical symptoms such as generalized lymphadenopathy and polyclonal hypergammaglobulinemia. In terms of histology based on immunohistological staining, the structure of the lymph node is found to have increases in polymorphic tumor cells and inflammatory cells such as reactive lymphocytes and eosinophils and is associated with an increase in high endothelial venules and follicular dendritic cells. B-cell immunoblasts are also present in the lymph node, which are often EB-virus-positive. The tumor cells are usually CD4-, CD10-, PD1- or CXCL13-positive.

Focusing on gene expression, the fact that the majority of the T-cell lymphomas are associated with rearrangement of T-cell receptor (TCR) will help with diagnosis. However, such TCR rearrangement may not be detected in AITL. On the other hand, rearrangement of the immunoglobulin that is usually detected in B-cell lymphomas is found in 30% of the cases. Accordingly, distinguishing AITL from other lymphomas such as B-cell lymphomas may sometimes be difficult. Based on such results of immunohistological staining patterns and characteristic gene expression profiles, the normal counterpart of the AITL tumor cell is considered to be one form of helper T-cells called follicular helper T-cell (TFH).

Meanwhile, peripheral T-cell lymphomas not otherwise specified (PTCL-NOS) account for 30% of the T-cell lymphomas. This disease name is used for peripheral T-cell lymphomas that have no feature characteristic enough to be diagnosed as specific peripheral T-cell lymphomas, and represents more heterogeneous disease concept in that they lack features as an independent disease group. Some of PTCL-NOS express a TFH marker, and may have morphological characteristic of AITL. There is no certain opinion about whether such marginal cases should be diagnosed as AITL or PTCL-NOS. At this point, the diagnosis depends on the principle of individual pathologists.

As described above, AITL (or AITL-like PTCL-NOS) is often difficult to be distinguished from other lymphomas such as B-cell lymphomas or from reactive changes. Therefore, an objective diagnostic method for distinguishing these diseases has been required in clinical practice and clinical research.

As pathological conditions of AITL in terms of molecular biology, gene mutations in TET2, IDH2 and DNMT3A have recently been identified, and mutations in the same genes, although less frequently, have also been reported in the cases of PTCL-NOS. However, since all of these gene mutations are also observed in myeloid tumors, they do not seem to contribute to a pathological image that is characteristic of AITL. Thus, a gene mutation specific to AITL had not been reported.

PRIOR ART DOCUMENTS

Non-Patent Documents

Non-patent Document 1: Blood. 2007 Jun. 1; 109(11):4952-63

Non-patent Document 2: J. Clin. Oncol. 2013 Jan. 10; 31(2):240-6

Non-patent Document 3: Blood. 2012 Aug. 16; 120(7): 1466-9

Non-patent Document 4: N. Engl. J. Med. 2012 Jan. 5; 366(1):95-6

SUMMARY OF THE INVENTION

Problems to be Solved by the Invention

The present invention aims at providing a method for detecting a T-cell lymphoma using a mutation in RHOA gene as an indicator.

Means for Solving the Problems

In order to solve the above-described problem, the present inventors have gone through keen examination, as a result of which found that the mutation of the 50th nucleotide among the nucleotide sequence of RHOA gene obtained from a subject was relevant to T-cell lymphoma, in particular AITL, thereby accomplishing the present invention.

Thus, the present invention is as follows.

(1) A method for detecting a T-cell lymphoma comprising the steps of: analyzing a gene mutation of at least one nucleotide selected from the group consisting of the 50th, the 331st, the 334th and the 482nd nucleotides or a gene mutation of the 49th to 51st nucleotides among the nucleotide sequence of RHOA gene collected from a subject; and correlating the result of said analysis with a T-cell lymphoma.

(2) The method according to (1) above, wherein a T-cell lymphoma is detected such that a T-cell lymphoma or a risk of a T-cell lymphoma is determined to exist when the gene mutation of the 50th nucleotide is G/T heterozygous or T/T homozygous, when the gene mutation of the 331st nucleotide is C/T heterozygous or T/T homozygous, when the gene mutation of the 334th nucleotide is A/G heterozygous or G/G homozygous, when the gene mutation of the 482nd nucleotide is C/A heterozygous or A/A homozygous or when the 49th to 51st nucleotides are deleted.

(3) The method according to (1) above, wherein the T-cell lymphoma is an angioimmunoblastic T-cell lymphoma or a peripheral T-cell lymphoma not otherwise specified.

(4) An oligonucleotide comprising a sequence of at least 10 nucleotides including the 50th, the 331st, the 334th or the 482nd nucleotide among the nucleotide sequence of RHOA gene or a sequence complementary thereto.

(5) The oligonucleotide according to (4) above, having a length of 10-579 nucleotides.

(6) A kit for detecting a T-cell lymphoma, comprising the oligonucleotide according to either one of (4) and (5) above.

Effect of the Invention

The present invention provides a method and a kit for detecting a T-cell lymphoma. Use of the method of the present invention can reveal the presence of a novel gene mutation characteristic to AITL and can conveniently and reliably detect or diagnose about 70% of AITL patients. Therefore, the method of the present invention is useful for detecting a T-cell lymphoma, understanding a pathological condition, diagnosing and developing a molecular-targeted therapy.

MODES FOR CARRYING OUT THE INVENTION

Figure 1:
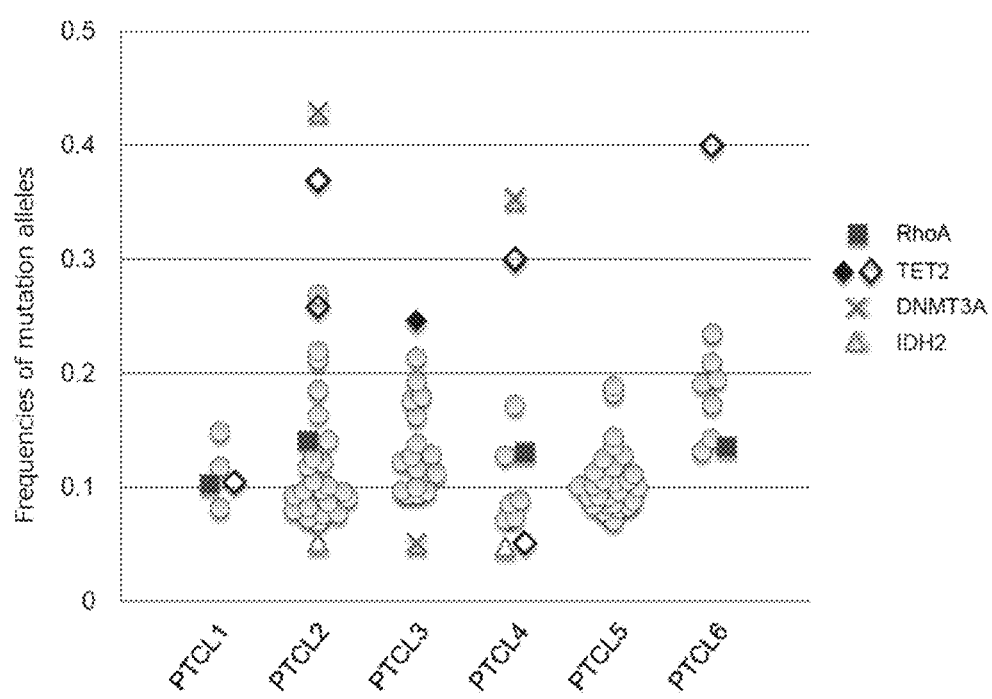
FIG. 1 A diagram showing frequencies of mutant alleles.

Hereinafter, the present invention will be described in detail. The present invention is a method for detecting a T-cell lymphoma comprising the steps of: analyzing a gene mutation of at least one nucleotide selected from the group consisting of the 50th, the 331st, the 334th and the 482nd nucleotides or a gene mutation of the 49th to 51st nucleotides among the nucleotide sequence of a gene coding for RHOA (also referred to as RHOA gene) collected from a subject; and correlating the result of said analysis with a T-cell lymphoma of the subject.

In addition, the present invention is a method for detecting a T-cell lymphoma comprising the steps of: analyzing the presence or the absence of a mutation of the 17th, the 111st, the 112nd or the 161st amino acid residue among the amino acid sequence of RHOA protein collected from a subject; and correlating the result of said analysis with a T-cell lymphoma of the subject.

Herein, the term "detect" means, by associating a mutation in a RHOA gene or a RHOA protein with a phenotype, to infer, determine, determine or diagnose that a T-cell lymphoma or a risk of T-cell lymphoma exists if there is a RHOA gene mutation or a RHOA protein mutation. In addition, the terms "the 50th", "the 331st", "the 334th" and "the 482nd" in the above-mentioned nucleotide sequence as well as the terms "the 17th", "the 111st", "the 112nd" and "the 161st" in the amino acid sequence represent the positions of the nucleotides and the amino acid residues targeted for the analysis by numbers in the full-length sequences of the RHOA gene and the RHOA protein, respectively. Therefore, even if a RHOA gene or a RHOA protein that is used for the actual analysis is, for example, a partial fragment that is shorter than the full-length sequence, the targeted positions remain to be represented by the above-mentioned numbers.

The present inventors found that the genotype of the 50th nucleotide of RHOA gene derived from a AITL or PTCL-NOS patient was G/T heterozygous or T/T homozygous, or the three nucleotides, i.e., 49th to 51st nucleotides, were deleted. The present inventors also found that the genotypes of the 331st, the 334th and the 482nd nucleotides of RHOA gene derived from an AITL or PTCL-NOS patient were C/T heterozygous or T/T homozygous, A/G heterozygous or G/G homozygous, or C/A heterozygous or A/A homozygous, respectively. Accordingly, the present invention relates to a method for assessing a T-cell lymphoma in an individual using substitution of the 50th nucleotide of RHOA gene (c.G50T (G17V in the amino acid sequence)), substitution of the 331st nucleotide (c.C331T (P111S in the amino acid sequence)), substitution of the 334th nucleotide (c.A331G (I112V in the amino acid sequence)), and substitution of the 482nd nucleotide (c.C482A (A161E in the amino acid sequence)), as well as deletion of the three nucleotides, i.e., the 49th to 51st nucleotides, as an indicator.

The positions of the mutations of RHOA gene in the cases of AITL are concentrated to a specific region and very specific to AITL among the malignant lymphomas (Examples, Table 2). Thus, the above-mentioned mutations can be used as basic information to be applied to diagnosis and treatment of AITL. According to the present invention, such mutations have been confirmed to be able to be specifically and sensitively detected in DNA from an analyte (tissue, blood, etc.) of a subject.

1. RHOA Gene and RHOA Protein

According to the present invention, a gene and a protein used for detection are RHOA gene and RHOA protein, respectively. RHOA (ras homolog family member A) gene is localized in the 3p21.3 region of the human chromosome 3, and is a gene coding for RHOA, a protein that belongs to Rho family of low-molecular-weight G protein. For example, human RHOA gene is represented by SEQ ID NO:1 while RHOA protein consists of the amino acid sequence represented by SEQ ID NO:2. The nucleotide sequence information of human RHOA gene and the amino acid sequence information of RHOA protein can be acquired, for example, from Accession No. NM_001664 (SEQ ID NOS:1 and 2).

2. Gene Mutation Marker

The information of the RHOA gene mutation targeted for an analysis according to the present invention is the mutation of the 50th nucleotide in the nucleotide sequence of RHOA gene (the 50th nucleotide in the nucleotide sequence represented by SEQ ID NO:1), which is referred to as "c.G50T". c.G50T results substitution of valine for glycine (Gly17Val or G17V) at position 17 in the amino acid sequence of RHOA protein (the 17th amino acid residue in the amino acid sequence represented by SEQ ID NO:2). In addition, the information of the RHOA gene mutation is also the mutation of the 331st nucleotide in the nucleotide sequence of RHOA gene (the 331st nucleotide in the nucleotide sequence represented by SEQ ID NO:1), the mutation of the 334th nucleotide (the 334th nucleotide in the nucleotide sequence represented by SEQ ID NO:1) and the mutation of the 482nd nucleotide (the 482nd nucleotide in the nucleotide sequence represented by SEQ ID NO:1), which are referred to as "c.C331T", "c.A334G" and "c.C482A", respectively. "c.C331T", "c.A334G" and "c.C482A" result substitution of serine for proline (Pro111Ser or P111S) at position 111 in the amino acid sequence of RHOA protein (the 111st amino acid residue in the amino acid sequence represented by SEQ ID NO:2), substitution of valine for isoleucine (Ile112Val or I112V) at position 112 in the amino acid sequence of RHOA protein (the 112nd amino acid residue in the amino acid sequence represented by SEQ ID NO:2), and substitution of glutamic acid for alanine (Ala161Glu or A161E) at position 161 in the amino acid sequence of RHOA protein (the 161st amino acid residue in the amino acid sequence represented by SEQ ID NO:2), respectively. Moreover, according to the present invention, deletion of the 49th to 51st nucleotides in the nucleotide sequence of RHOA gene (the 49-51st nucleotides in the nucleotide sequence represented by SEQ ID NO:1) is caused. This deletion is referred to as "c.49_51del" (deletion of the amino acid residue at position 17 of the amino acid sequence represented by SEQ ID NO:2 (p.17_17del)).

Here, according to Rhotekin binding analysis, a cell with RHOA that has a valine residue as the amino acid at position 17 was found to have a decreased function in becoming an active-form RHOA (that can bind to Rhotekin) as compared to a cell with only wild-type RHOA having a glycine residue. Specifically, mutant RHOA has lower GTP-binding ability than wild-type RHOA, and thus is less likely to take a GTP-binding form. Furthermore, analysis of the actin polymers revealed that a cell with mutant RHOA had reduced actin polymerization ability while a reporter assay using a serum responsive factor response element (SRF-RE) also revealed that mutant RHOA suppresses SRF transcriptional activity of wild-type RHOA.

According to the present invention, gene mutations principally include a single nucleotide mutations of the 50th, the 331st, the 334th and the 482nd nucleotides as well as insertion/deletion mutations in the nucleotide sequence of RHOA gene. An example of the deletion mutation includes deletion of the three nucleotides, i.e., 49th to 51st nucleotides, in the nucleotide sequence of RHOA gene.

According to the present invention, T-cell lymphomas targeted for detection are angioimmunoblastic lymphomas (AITL) and peripheral T-cell lymphomas not otherwise specified (PTCL-NOS).

The above-mentioned mutations of RHOA gene and RHOA protein can be utilized as a marker for assessing a T-cell lymphoma of a subject. Specifically, by analyzing these mutations, whether or not a T-cell lymphoma, particularly AITL, exists can be assessed.

c.G50T mutation (G17V mutation of the amino acid sequence), c.C331T mutation (P111S mutation of the amino acid sequence), c.A334G mutation (I112V mutation of the amino acid sequence) and c.C482A mutation (A161E mutation of the amino acid sequence) as well as $Del_{49\text{-}51}$ found according to the present invention are determinants for T-cell lymphomas. Taking the case of the 50th nucleotide of the analyzed RHOA gene and the 17th amino acid sequence of RHOA protein as an example, the correlation between the mutation and the phenotype is such that AITL or PTCL-NOS or a risk of AITL or PTCL-NOS can be determined to exist when the gene mutation is G/T heterozygous or T/T homozygous and the amino acid sequence has G17V mutation (the same also applies to the nucleotides and the amino acids at other positions). According to a statistical analysis conducted by the present inventors using 158 cases, the probability of AITL or PTCL-NOS is 50% or higher, preferably 60%, more preferably 70%, and still more preferably 80% or higher. Likewise, when the gene mutation of the 331st, the 334th or the 482nd nucleotide of the analyzed RHOA gene is C/T heterozygous or T/T homozygous, A/G heterozygous or G/G homozygous, or C/A heterozygous or A/A homozygous, respectively, AITL or PTCL-NOS or a risk of AITL or PTCL-NOS can be determined to exist. Furthermore, when the three nucleotides, i.e., the 49th to 51st nucleotides, of the analyzed RHOA gene are deleted, AITL or PTCL-NOS or a risk of AITL or PTCL-NOS can be determined to exist.

Regarding distinction between AITL and PTCL-NOS, for example, when there is c.G50T mutation, a risk of AITL can be determined or inferred to exist at a probability of 50% or higher, preferably 60% or higher, more preferably 70% or higher, and still more preferably 80% or higher.

Once a risk of a T-cell lymphoma (AITL or PTCL-NOS) is determined to exist by the present invention, a therapeutic agent for the T-cell lymphoma can be administered to the patient. Accordingly, the present invention provides a method for treating a T-cell lymphoma, comprising a step of administering a therapeutic agent for the T-cell lymphoma to the patient who has been determined to have the above-described risk of T-cell lymphoma (AITL or PTCL-NOS).

Examples of a therapeutic agent for a T-cell lymphoma include, but not particularly limited to, CHOP therapy (cyclophosphamide, doxorubicin, vincristine, prednisolone).

Usage upon administration of the above-described therapeutic agent is not limited but usually parenteral or oral usage is employed.

In the case of preparing an oral solid formulation, the formulation may be used alone or suitably in combination with an excipient, a binder, a disintegrator, a lubricant, a colorant, a flavoring agent or the like to form, for example, a tablet, a coated tablet, granules, fine granules, a powdered agent, a capsule or the like.

In the case of preparing a parenterally administered formulation such as an injection agent, a pH adjuster, a buffer, a suspending agent, a solubilizing agent, a stabilizer, a tonicity agent, a preserving agent or the like may be added, as necessary, so as to form, for example, a formulation as an intravenous, subcutaneous or intramuscular injection agent, which may be provided in a unit dosage ampule, a multi-dose container or the like. If necessary, it may be made into a freeze-dried product.

The given dose of the above-described therapeutic agent may vary according to the degree of the symptom, age, sex and weight of the patient, the administration method, the administration period, the dosing interval and the like. For example, but without particular limitation, in the case of CHOP therapy, cyclophosphamide is administered for 300-750 mg per body surface area on Day 1, doxorubicin is administered for 25-50 mg per body surface area on Day 1, vincristine is administered for 0.7-1.4 mg per body surface area on Day 1, and prednisolone is administered for 50-100 mg for five days from Day 1 through Day 5.

Now, according to the method of the present invention, specimens obtained from multiple subjects are used to analyze the mutations. Therefore, in order to detect a T-cell lymphoma of an individual subject, the position where the individual exists or belongs to across the entire results can be examined by a statistical analysis of Spearman's rank-correlation coefficients or the like with respect to a quantitative analysis of gene mutations in genomic DNA by an allele specific PCR method to find out the possibility of a T-cell lymphoma in the individual subject. Moreover, an analysis of the correlation between the mutation and the phenotype (T-cell lymphoma) may be carried out beforehand for a predetermined number of subjects (primary population) so that the resulting measured values can be used as basic data. This basic data can be compared with a mutation in a single or multiple subjects targeted for detection, for correlating with the phenotype, i.e., T-cell lymphoma.

The subject-derived data measured as described above can be integrated into the above-described primary population to reprocess the data of the mutation information and the T-cell lymphoma risk level so as to increase the number of the targeted subjects (general population), thereby improving accuracy of the analysis.

3. Method for Detecting Mutation

A genome sample from a subject for detecting the above-described mutation can be extracted from a biological specimen such as blood, saliva, skin, lymph node, bone marrow or the like but not limited thereto as long as a genome sample can be collected. Methods for extracting and purifying genomic DNA are well known. For example, a sample can be extracted from an analyte such as blood or saliva collected from human using a kit such as QIAmp DNA mini kit, QIAmg DNA FFPE Tissue kit (QIAGEN), Wizard (registered trademark) Genomic DNA Purification Kit (Promega) or NucleoSpin (registered trademark) series kit (Takara Bio). In the case of the present invention, since the mutations exist in the coding region (open reading frame) of RHOA protein, mRNA or total RNA may be extracted instead of genomic DNA.

Hereinafter, one exemplary method for detecting a gene mutation and an amino acid mutation in the above-described test sample will be illustrated.

(1) Detection Using PCR Technique

In order to amplify the test sample by PCR, high-fidelity DNA polymerase, for example, KOD-Plus-neo polymerase (TOYOBO) is preferably used, although it is not limited thereto. The primers used are designed and synthesized such that the gene mutation is included at an arbitrary site of the primers to amplify the targeted mutation moiety in the test sample.

At the end of the amplification reaction, the amplified product is detected to determine the presence or the absence of the mutation. For example, TaqMan PCR technique is a method that utilizes PCR reaction with a fluorescently-labeled allele-specific oligonucleotide and Taq DNA polymerase. An allele-specific oligonucleotide (named TaqMan probe) used in the TaqMan PCR method can be designed based on the above-described gene mutation information. Alternatively, fluorescently-labeled nucleotides can be integrated into the amplified product using Sybr Green PCR method upon amplification with allele-specific primers to quantitatively determine the mutant gene.

(2) Detection by Nucleotide Sequence Determination Method

According to the present invention, a mutation can also be detected by direct sequencing. As a sequencer used for the nucleotide sequence determination, commercially available HiSeq system, MiSeq system (Illumina), ABI series (Life Technologies), PGM system (Life Technologies) or the like may be used.

(3) Detection with DNA Microarray

A DNA microarray has nucleotide probes fixed on a support, and includes a DNA chip, a microchip, a bead array and the like. First, a polynucleotide of a test sample is isolated, amplified by PCR and labeled with a fluorescent reporter group. Subsequently, the labeled DNA/mRNA and total RNA are incubated with the array. Then, this array is inserted into a scanner to detect the hybridization pattern. The hybridization data is collected as luminescence from the fluorescent reporter groups bound to the probe array (in other words, incorporated into the target sequence). A probe that has exact match with the target sequence would produce a stronger signal than a probe with a moiety that differ from the target sequence. Since the sequences and the locations of the respective probes on the array are known, the sequence of the targeted polynucleotide that was allowed to react with the probe array can be determined due to complementation.

(4) Detection of Gene Mutation by Invader Assay

Invader assay is a method for detecting gene polymorphism by hybridizing an allele-specific oligonucleotide with a template. This method can be used for the detection of the mutation according to the present invention. A kit for carrying out the invader assay is commercially available. According to this method, a gene mutation can easily be detected.

(5) Detection of Amino Acid Mutation

In order to analyze an amino acid mutation of RHOA protein according to the present invention, RHOA protein obtained from a sample such as a blood sample or a surgically resected analyte of a subject is analyzed for "the 17th", "the 111st", "the 112nd" or "the 161st" amino acid sequence through a direct sequencing method of the amino acid sequence to detect whether or not the amino acid has been mutated. Moreover, the mutation can also be detected based on an analytical method that utilizes an electrophoresis method such as western blotting and pull-down assay.

RHOA protein can be obtained from the above-described sample, for example, by suitably combining techniques well known in this field, such as protein solubilization with a surfactant, dialysis, gel filtration, ion-exchange chromatography, affinity chromatography and the like.

4. Oligonucleotide

The present invention provides an oligonucleotide containing a gene mutation that specifically hybridizes with a DNA fragment containing the above-described gene mutation. The term "hybridize" means that DNA pairs are formed during a course of general PCR or hybridization. Accordingly, hybridization conditions can be determined using a commercially available PCR reagent or a hybridization reagent.

Table 1 shows a nucleotide sequence of the coding region including c.G50T, c.C331T, c.A334G and c.C482A mutations as well as Del49-51 deletion in the nucleotide sequence of RHOA gene (SEQ ID NO:3), where the 50th, the 331st, the 334th and the 482nd nucleotides are boxed and deletion "c.49_51del" is indicated with a crossed line.

TABLE 1

Nucleotide sequence containing mutation sites

SEQ ID NO: 3 atgg ctgccatccg gaagaaactg gtgattgttg gtgatggagc ctgtg g/t aaag acatgcttgc tcatagtctt cagcaaggac TABLE 1 -continued Nucleotide sequence containing mutation sites cagttcccag aggtgtatgt gcccacagtg tttgagaact atgtggcaga tatcgaggtg gatggaaagc aggtagagtt ggctttgtgg gacacagctg ggcaggaaga ttatgatcgc ctgaggcccc tctcctaccc agataccgat gttatactga tgtgtttttc catcgacagc cctgatagtt tagaaaacat cccagaaaag tggaccccag aagtcaagca tttctgtccc aacgtg c/t cc a/g tcatcctggt tgggaataag aaggatcttc ggaatgatga gcacacaagg cgggagctag ccaagatgaa gcaggagccg gtgaaacctg aagaaggcag agatatggca aacaggattg gcgcttttgg gtacatggag tgttcag c/a aa agaccaaaga tggagtgaga gaggttttg aaatggctac gagagctgct ctgcaagcta gacgtgggaa gaaaaaatct gggtgccttg tcttgtga In Table 1, "g/t" means that "G" has been mutated into "T", "c/t" means that "C" has been mutated into "T", "a/g" means that "A" has been mutated into "G", and "c/a" means that "C" has been mutated into "A". The present invention provides oligonucleotides having at least 10 nucleotides, for example, 10-579 nucleotides, preferably 10-100 nucleotides and more preferably 10-50 nucleotides, including the above-described mutation sites of the nucleotide sequence (SEQ ID NO:1) of RHOA gene (c.G50T, c.C331T, c.A334G, c.C482A). These oligonucleotides can be used as a probe or PCR primers for detecting a T-cell lymphoma. A T-cell lymphoma is detected using the above-described c.G50T, c.C331T, c.A334G or c.C482A mutation, or c.49_51 del mutation as an indicator. The probe or PCR primers for detecting a T-cell lymphoma will be described hereinbelow. A method for acquiring a genomic DNA sample from a test subject is as described above.

Oligonucleotides used as primers and/or a probe in the present invention are oligonucleotides of at least 10 nucleotides that are designed to contain an oligonucleotide including the 50th, the 331st, the 334th or the 482nd nucleotide of the nucleotide sequence of RHOA gene (for example, SEQ ID NO:1). The lengths of the oligonucleotides are not particularly limited as long as they have at least 10 nucleotides, for example 10-579 nucleotides, preferably 10-100 nucleotides and still more preferably 10-50 nucleotides. An oligonucleotide of the present invention can be obtained by a common chemical synthesis based on the nucleotide sequence represented by SEQ ID NO:1. The present invention also comprises complementary strands (complementary sequences) of these sequences. In addition, according to the present invention, the oligonucleotides can be designed and synthesized based on the nucleotide sequence information represented by SEQ ID NO:3 shown above. In this case, although the oligonucleotides may be designed such that the mutation sites are present at the 5' end or the 3' end of the nucleotide sequences, it is not limited thereto and the sites may be present at a location inside of the 5' or 3' end.

The prepared oligonucleotide can be used as a probe so that whether or not the probe has hybridized with the test DNA, namely, the presence or the absence thereof, can be utilized to determine or detect the mutation. The probe may be used, for example, as TaqMan (registered trademark) probe.

Preferably, the probe is designed to contain the 50th nucleotide of the nucleotide sequence represented by SEQ ID NO:1 along with the nucleotides upstream or downstream from the 50th nucleotide. The probe designed and synthesized as such is referred to as probe 50, where an allele having "G" (normal sequence) as the 50th nucleotide is referred to as "allele G", and an allele having "T" (sequence having mutation of the 50th nucleotide) is referred to as "allele T". Hybridization is carried out under conditions such that probe 50 hybridizes with the sequence of allele G but not with the sequence of allele T. Since probe 50 hybridizes with DNA having the sequence of allele T, whether the allele is G or T can be determined (detected) according to the presence or the absence of the band.

When oligonucleotides are designed as primers for detecting allele 50, oligonucleotides are designed from the upstream side of the 50th nucleotide as well as from the downstream side of the 50th nucleotide. By doing so, fragments amplified by PCT and detected will have different sizes according to the presence or the absence of the mutation and the thus mutation can be detected according to the difference between the sizes of the fragments. The primers are designed such that the lengths thereof is at least 15 nucleotides, preferably 15-30 nucleotides and still more preferably 18-24 nucleotides. Of course, the design of the primers is not limited to a region within the 50 nucleotides upstream and downstream from the 50th nucleotide described above, and may also suitably be selected from a region of the template DNA based on the sequence of the genomic DNA such that the amplified fragment will be 1000 bp or less, preferably 500 bp or less and still more preferably 200 bp or less (for example, 50-100 bp). In the same manner as the 50th nucleotide described above, oligonucleotides may be designed to contain the 331st, the 334th or the 482nd nucleotide along with the nucleotides upstream and downstream from said nucleotide.

Although the oligonucleotide primers and the oligonucleotide probe designed as described above can chemically be synthesized by a known procedure and method, they are generally synthesized by using a commercially available chemical synthesizer. The probe may also be added with an appropriate fluorescent label (for example, FAM, VIC, etc.) beforehand so as to automate the procedure.

5. Kit

The present invention provides a kit for detecting a T-cell lymphoma. The kit of the present invention comprises one or more components necessary for carrying out the present invention. For example, a kit of the present invention may comprise an oligonucleotide of the present invention, an enzyme buffer, dNTP, a reagent for control (for example, a tissue sample, targeted oligonucleotides for positive and negative controls, etc.), a reagent for labeling and/or detection, a solid phase support, instructions and the like. Alternatively, a kit of the present invention may also be a partial kit that contains some of the necessary components, in which case the user can prepare the rest of the components.

A kit of the present invention can also be provided as a microarray that has the above-described oligonucleotides fixed on a support. A microarray has the oligonucleotide of the present invention fixed on a support, and may include a DNA chip, a microchip, a bead array or the like.

Preferably, the kit of the present invention comprises an oligonucleotide that specifically hybridizes with a DNA fragment containing the mutation of RHOA gene.

In order to determine a gene mutation with the kit of the present invention, for example, the above-described DNA containing RHOA gene is isolated from blood, saliva, body cavity fluid (pleural effusion, ascitic fluid, spinal fluid, etc.), bone marrow fluid, a tumor analyte, a fixed specimen prepared therefrom or the like upon diagnosing the disease, and the isolated DNA is allowed to react with the oligonucleotide included in the kit to determine the genotype.

Based on the determined genotype and gene mutation, the presence of a T-cell lymphoma (particularly AITL) or a risk of a T-cell lymphoma is determined.

Hereinafter, the present invention will be described more specifically by means of examples. The present invention, however, should not be limited to these examples.

Example 1

1. Summary

According to this example, 3 AITL cases and 3 PTCL-NOS cases were analyzed by whole-exome sequencing method (WES). With respect to the entire regions of RHOA gene that was found to have mutations by WES as well as TET2, IDH1/2 and DNMT3A genes which had been reported of their highly frequent mutations, 80 cases were analyzed by targeted sequencing method. Furthermore, with respect to the highly frequent mutated site of RHOA, 78 cases were analyzed by hotspot sequencing method. Thus, a total of 158 cases were analyzed. WES revealed somatic mutations of RHOA gene for 3 AITL cases and 1 PTCL-NOS case, where all of the mutations were those that would result G17V substitution in the amino acid sequence.

Additional analysis was performed for more number of cases. As a result, mutations were found in 71.2% of RHOA, 85.4% of TET2, 29.2% of IDH2 and 29.2% of DNMT3A for AITL while mutations were found in 16.5% of RHOA, 50.0% of TET2, 0% of IDH2 and 28.1% of DNMT3A for PTCL-NOS, although at a frequency lower than AITL. Interestingly, TET2 mutation was found in almost all of the RHOA mutation cases. For some of the cases, TET2 mutation was also found in the bone marrow sample that had no lymphoma infiltration but RHOA mutation was not observed. This means that RHOA is more specific to the onset of a T-cell lymphoma. RHOA G17V mutant is less likely to take a GTP-binding form than a wild type. Also, according to a reporter analysis for a serum-responsive factor response element (SRE), RHOA G17V mutant suppressed the function of the wild-type in a dominant negative manner.

In the present example, RHOA G17V mutation was newly identified as genetic abnormality in a T-cell lymphoma. From the observation that functionally deficient mutations were found to be highly frequent, there is a possibility that functional depression of RHOA may play an important role in the pathological conditions of a T-cell lymphoma, in particular AITL.

2. Experiments (1) Patients and DNA and Pathological Samples

Analytes from patients with AITL, PTCL-NOS and, as controls, other peripheral T-cell lymphoma, B-lymphoma and bone myeloid tumor were used. Experiment was carried out with approval from the ethical committee of each participating organization. High-molecular weight genomic DNAs were extracted from a fresh frozen analyte of a biopsy tissue such as a lymph node and an analyte fixed by PLP method (a method that uses a fixative containing paraformaldehyde, metaperiodic acid and lysine) with QIAmp DNA mini kit or QIAmp DNA FFPE Tissue kit (QIAGEN), respectively. For hotspot sequencing, DNA was extracted from a sample fixed in formalin and embedded in paraffin (FFPE sample) with QIAmp DNA FFPE Tissue kit (QIAGEN). As control samples, DNA was extracted from a mononuclear fraction isolated from an oral mucosa sample or a fine-needle aspiration bone marrow sample without lymphoma infiltration.

(2) Whole-Exome Sequencing (WES)

A whole-exome library was prepared from non-amplified tumor and normal pair analyte DNAs with SureSelect Exome Capture kit 50 Mb or V4 kit, and analyzed with HiSeq2000. The mutations identified by whole-exome sequencing method (WES) were analyzed by deep sequencing method after amplifying the marginal region including the site of mutation by PCR method using DNA amplified with REPLI-g mini kit containing a whole-genome amplification enzyme.

According to targeted sequencing of all exon regions of RHOA, TET2, IDH1/2 and DNMT3A, said regions were enriched with SureSelect bait library (Agilent) using DNAs amplified or not amplified with REPLI-g mini kit and analyzed with HiSeq2000. With respect to the G17V RHOA region, analytes from patients with AITL/PTCL-NOS and other hematopoietic organ tumors extracted from FFPE (FFPE stands for formalin-fixed, paraffin-embedded) specimens were also analyzed, using deep sequencing method and Sanger method. The genome sequence data is available from European Genome-Phenome Archive. The tumor DNAs were extracted from biopsy samples having lymphoma cell infiltration. As normal control, DNA extracted from bone-marrow cell without lymphoma cell infiltration or oral mucosa was used. Whole-exome capture was carried out by hybridizing sonicated genomic DNAs with a cDNA library synthesized on magnet beads (SureSelect Human All Exon 50 Mb or V4 kit, AgilentTechnology). The captured region was analyzed by a standard protocol with 100 bp pair ends using HiSeq2000. Candidates for somatic mutation were analyzed with respect to the results from whole-exome sequencing by the following analysis method.

(3) Detection of Somatic Mutation Based on Results from Whole-Exome Sequencing

Somatic mutation was analyzed using Genomon-exome. The candidates of somatic gene were detected by slightly changing the published algorithm. Specifically, the number of reads containing SNV and insertion/deletion was calculated with SAMtool, the null hypothesis that the tumor and control samples equally have mutations was tested by Fisher's exact test (two-sided test). A candidate of somatic mutation was detected if the p-value was less than 0.01, mutation was detected in both directions and the allele frequency of the normal control mutation was 0.1 or less. Eventually, a list was made by leaving out dpSNP131, 100 genome and SNPs of the SNP database built based on the analysis of the original 180 cases.

(4) Deep Sequencing Method for Verifying Whole-Exome Analysis

The genomes of the tumor and control samples were amplified using REPLI-g mini kit. Regions containing the somatic mutation were amplified by genome PCR method using KOD-Plus-neo enzyme. Primers were attached with NotI linker. PCR products were mixed and DNA was purified with a PCR purification kit and then cleaved with NotI. DNA was again purified, then 1 µg of the resultant was reacted with T4DNA ligase for 5 hours, and thereafter cleaved with Covaris into an average of around 150 bp. A library was prepared according to a modified Illumina's pair-end library protocol, and analyzed according to a standard protocol of 100 bp pair ends using HiSeq2000.

The reads were each aligned to the target sequence of the PCR product to match the about 100 readout nucleotides with the sequence to be read. The mapping information was converted from .pls format to .sam format using original my_psl2sam scrip. Upon conversion, the script of the original method was partially modified in order to add information of the pair ends. Only suitably mapped reads were analyzed. Cases where the read was mapped along a number of regions, where there are more than 4 nucleotide mismatches, and where there is a sequence with 10 or more mismatched nucleotides were excluded. Analysis with Estimation CRME was conducted in order to remove a strand-specific error and a cycle-specific error. The strand-specific mismatch probability was calculated for each nucleotide variant with respect to both strands for cycles 11-50. Somatic mutation was determined to exist when SNV was equal to or higher than 2%.

(5) Functional Analysis of RHOA G17V Mutant

Wild-type or G17V-mutant-type was transfected into NIH-3T3 cells to use the cells for analyzing the amount of GTP-binding-type (active-type) RHOA by Rhotekin pull down assay (Cytoskeleton). The RHOA activity was analyzed by luciferase reporter assay using serum responsive factor response element (SRE).

(6) Statistical Analysis 79 genes, mainly genes screened by WES method and genes that have been reported to have mutations in other tumors and highly possible to show mutation in a T-cell lymphoma as well, were selected and analyzed by target sequencing. Similar to WES, DNAs were sonicated and the regions in question were enriched by SureSelect target enrichment system designed for all exon regions of the 79 genes. Thereafter, they were subjected to sequence analysis with HiSeq2000.

The sequenced reads were aligned to hg19 using the default parameters of BWA version 0.5.8. Poor-quality reads and nucleotide information were excluded. The frequency of SNV or insertion/deletion in each genome region was calculated with SAMtool. When total of 10 or more reads with mutations in 6 or more reads were read, all of the nucleotide substitutions having allele frequency of 0.02 or higher were extracted and annotated using ANNOVAR software. Mutations that did not result amino acid substitution and mutations that were registered as SNP in dpSNP131, 100 genome project (May 21, 2012) and the original database were excluded. SNVs were analyzed by Sanger method for confirmation. When SNV was less than 5%, Ion Torrent sequencer was used for confirmation.

(7) Analysis of RHOA G17V Mutation by Hotspot Sequencing

For additional 78 cases, regions containing RHOAc.50T p.G17V hotspot were subjected to genome PCR. Tag sequences each having six nucleotides were inserted into the PCR primers for distinguishing the samples. The PCR product was analyzed with HiSeq2000 as described above. Mutation was determined to exist when conversion from G to T was equal to or higher than 2.0%.

(8) Antibody

For western blot, mouse anti-RHOA antibody (Cytoskeleton), mouse anti-β-actin antibody (Sigma), mouse anti-Flag antibody (Sigma), mouse anti-myc antibody (MBD) and rabbit anti-mouse IgG antibody/HRP (Dako) were used.

(9) Cell Lines and Gene Transfer

NIH3T3 cells and HEK293 cells were cultured in an incubator at 37° C. in 5% $CO_2$. DMEM (D6046: Sigma) added with fetal bovine serum and penicillin/streptomycin to 10% and 1%, respectively, was used as a culture solution. Gene transfer was carried out using a lipofection reagent FuGene6 (Roche) according to the attached protocol.

(10) Generation of Mutant and Preparation of Modified Gene cDNA of human RHOA was amplified from healthy human peripheral-blood mononuclear cell-derived cDNA using PCR method. RHOA (G14V), RHOA (G17V), and RHOA (T19N) mutations were generated with PrimeStar mutagenesis Basal Kit (Takara) according to the protocol. Moreover, cDNAs having Flag tag and c-Myc tag inserted into the N-terminus were prepared for wild-type RHOA and all of the mutant RHOA. All of these cDNAs were inserted into expression vector pEF-neo or retrovirus vector pGCDNsamIRE SGFP. The sequence was confirmed to be the one expected by sequencing.

(11) RHOA Activation Assay

RHOA activity analysis was carried out using RHOA activation assay kit (Cytoskeleton) according to the protocol. A cell lysate was allowed to react with GST-protein-fused Rho-binding domain (GST-RBD) fixed on glutathione sepharose beads at 4° C. for an hour. The resultant was washed twice with a lysis buffer and once with a wash buffer, subsequently dissolved in a laemmli buffer and boiled at 95° C. for 5 minutes. The resultant was subjected to electrophoresis with 12% SDS-PAGE gel to detect active-type RHOA by western blotting method using anti-RHOA antibody. A cell lysate prior to immunoprecipitation was similarly subjected to western blot to also detect the amount of whole RHOA protein.

(12) SRF-RE Reporter Assay

The activity of the serum response factor (SRF) was determined using pGL4.34 reporter vector (Promega). This vector is provided with an SRF response sequence (SRF-RE) which is designed to react in a SRF-dependent, TCF-independent pathway that occurs upon activation of RHOA. NIH3T3 cells were seeded into 24-well plate and 40 ng of pGL4.34 vector, 20 ng of pSRalpha gal vector and an indicated amount of RHOA expression plasmid shown in the figure per well were cotransfected into the cells. Following 48 hours of cultivation, the cells were lysed and the luciferase activity was determined using a luminometer. Simultaneously, β-gal activity was also determined to be used for standardization.

(13) Mutation-Specific Real-Time PCR Method for Detecting RHOA G17V Mutation

Genomic DNAs (43 AITL cases and 52 PTCL-NOS cases) were extracted from 47 PLP specimens and 48 frozen specimens. Allele-specific primers for detecting c.G50T of RHOA gene were designed following Wangkumhang's algorithm. Then, [mut] value and [WT] value were determined by real-time PCR using respective primer sets to calculate [mut]/([mut]+[WT]) value. The frequency of mutant alleles was determined by high-throughput sequencing using tag PCR and MiSeq (Deep sequencing method). Here, the [mut] value is an amount of mutant alleles quantitated by real-time PCR using mutation-specific primers while the [WT] value is an amount of mutant alleles quantitated by real-time PCR using wild-type-specific primers.

(14) Results (i) Novel Highly-Frequent Mutation of RHOA Gene (FIG. 1)

For 3 AITL cases and 3 PTCL-NOS cases, somatic mutations in protein-coding regions were analyzed by WES method. The analysis resulted an average depth of 20 or more (the number of reads in the same region is 20 times or more). Somatic mutations that imply 87 types of amino acid changes were detected, which were confirmed by Sanger method or deep sequencing. 79 cases of missense mutations, 5 cases of nonsense mutations, 2 cases of frameshift mutation and 1 case of non-frameshift deletion were confirmed. Only RHOA gene c.G50T mutation was reproducibly detected as a mutation by WES, for 3 AITL cases and 1 PTCL-NOS case, which results an amino acid sequence change of p.G17V.

FIG. 1 is a diagram that shows frequency of mutant alleles, showing gene abnormality found by whole-exome sequencing (WES) as well as TET2/IDH2/DNMT3A gene abnormality found by targeted sequencing for the cases subjected to WES.

Figure 2:
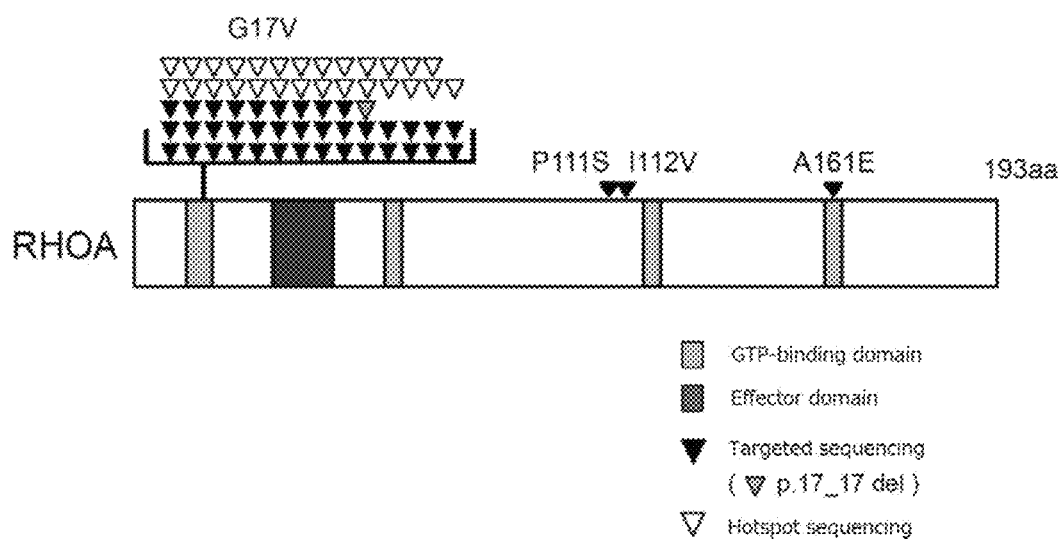
FIG. 2 A diagram showing mutations of RHOA genes from PTCL patients.

(ii) Frequencies of RHOA Mutations (Table 2, Table 3, FIG. 2)

Since key results were obtained by WES, additional samples were analyzed. For full-length RHOA gene, 80 cases were analyzed. RHOA mutations concentrated on G17V except for 4 cases. Mutations other than G17V were p.P111S, p.I112V, p.A161E and p.17_17del (Table 2, FIG. 2). Furthermore, for RHOA G17V, a total of 158 samples were analyzed. G17V mutation was observed in 52 out of 73 AITL cases (71.2%) and 14/85 (16.5%) PTCL-NOS samples (Table 3). With respect to G17V mutation, other hematopoietic organ tumor, specifically, 142 myeloid tumor cases, 91 B-cell tumor cases and 11 cases of other T-cell lymphoma were analyzed but G17V mutation was not detected (Table 3).

FIG. 2 is a diagram showing mutations in RHOA genes from PTCL patients.

TABLE 2

| Change of Transcript | AA Change | Type of Mutation | Number of Mutations |
|---|---|---|---|
| Target Sequencing (N = 80) | | | |
| c.G50T | p.G17V | Missense | 37 |
| c.C331T | p.P111S | Missense | 1 |
| c.A334G | p.I112V | Missense | 1 |
| c.C482A | p.A161E | Missense | 1 |
| c.49_51del | p.17_17del | Nonframeshift del | 1 |
| Hotspot Sequencing (N = 78) | | | |

TABLE 2-continued

| Change of Transcript | AA Change | Type of Mutation | Number of Mutations |
|---|---|---|---|
| c.G50T | p.G17V | Missense | 27 |
| Total (N = 158) | | | 68 |

Table 2 indicates mutations in RHOA genes found by targeted sequencing and hotspot sequencing, and shows that mutations in RHOA genes were concentrated to c.G50T (p.G17V).

TABLE 3

| Disease | Number of mutated cases (%) |
|---|---|
| [T cell malignancies] | |
| AITL*[1] | 52/73 (71.2) |
| PTCL-NOS | 14/85 (16.5) |
| with AITL features | 11/25 (44.0) |
| wo AITL features | 2/34 (5.9) |
| ND | 1/26 (3.8) |
| Other T cell malignancies | 0/11 (0) |
| [B cell malignancies] | |
| DLBCL | 0/44 (0) |
| FL | 0/19 (0) |
| Other B cell malignancies | 0/28 (0) |
| [Myeloid malignancies] | |
| AML | 0/89 (0) |
| MDS | 0/36 (0) |
| MPN | 0/14 (0) |
| MDS/MPN | 0/3 (0) |

Table 3 shows frequencies of RHOA gene in various hematopoietic organ tumors, where no RHOA gene mutation was found in tumors other than AITL and PTCL-NOS within the range analyzed this time.

Figure 3:
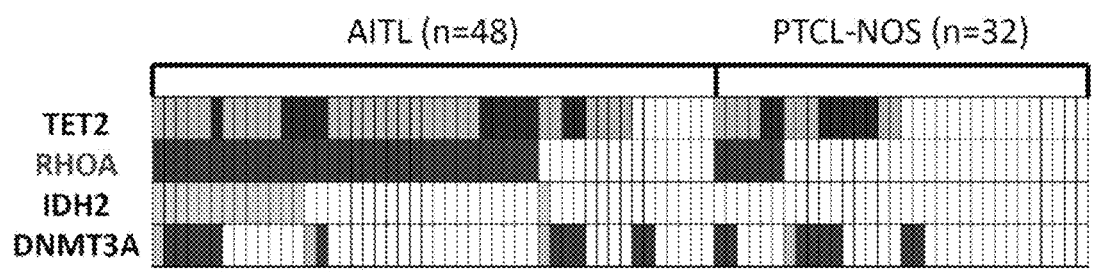
FIG. 3 A diagram showing mutation maps of PTCL samples.

(iii) Relationship Between RHOA Gene and Other Gene Mutations (Table 4, FIG. 3)

Next, relationship between RHOA mutation and other gene mutations was clarified.

FIG. 3 is a diagram showing mutation maps of T-cell lymphoma samples, showing relationship of gene abnormality among TET2, RHOA, IDH2 and DNMT3A.

TET2 mutation was found in 57 out of 80 cases, specifically, 41 out of 48 AITL cases (85.4%) and 16 out of 32 PTCL-NOS cases (50.0%). Similarly, IDH2 mutation existed in 14 out of 80 cases (17.5%). The mutation concentrated at R172. Interestingly, RHOA, TET2 and IDH2 had characteristic mutation patterns. Specifically, TET2 mutation was found in all of the RHOA-mutation-positive cases. Moreover, RHOA/TET2 mutation was found in most of the IDH2-mutation-positive cases. DNMT3A mutation was found in 23 out of 80 cases (28.8%). While cases with DNMT3A mutation are likely to also have TET2 mutation, there was no certain tendency in the presence or the absence of RHOA or IDH2 mutation.

TABLE 4

| | TET2 | RHOA | IDH2 | DNMT3A |
|---|---|---|---|---|
| Total | 57/80 | 39/80 | 14/80 | 23/80 |
| | (71.3%) | (48.8%) | (17.5%) | (28.8%) |
| AITL | 41/48 | 33/48 | 14/48 | 14/48 |
| | (85.4%) | (68.8%) | (29.2%) | (29.2%) |

TABLE 4-continued

|  | TET2 | RHOA | IDH2 | DNMT3A |
|---|---|---|---|---|
| PTCL-NOS | 16/32 (50.0%) | 6/32 (18.8%) | 0/32 (0%) | 9/32 (28.1%) |

Table 4 shows mutations in RHOA/TET2/IDH2/DNMT3A genes found by targeted sequencing.

(iv) RHOA G17V Mutation and Immunohistological Phenotype (Table 5)

Immunostaining was conducted for 59 PTCL-NOS cases with CD4, CD8, TIA1, and AITL markers, i.e., CD10, CD21 and PD1. RHOA mutation was found in 13 cases among them. For 25 cases, CD4 and at least one or more of the AITL markers were positive, among which RHOA mutation was found in 11 cases (44.0%). In the rest of the 34 cases, RHOA mutation was positive only in 2 cases. According to the present invention, RHOA mutation was found to be highly frequent in PTCL-NOS having closer property to AITL.

TABLE 5

| Sample ID | CD10 | PD-1 | CD21 + FDC | EBER + cells | CD4 | CD8 | TIA1 | TFH markers | RHOA mut |
|---|---|---|---|---|---|---|---|---|---|
| PTCL3 | − | + | − | + | + | − | − | + | 0 |
| PTCL6 | + | + | − | + | + | − | − | + | 1 |
| PTCL14 | − | + | − | + | + | − | − | + | 0 |
| PTCL40 | − | + | − | + | + | − | − | + | 0 |
| PTCL44 | − | + | − | + | + | − | − | + | 1 |
| PTCL49 | − | + | + | + | + | − | − | + | 0 |
| PTCL50 | + | + | − | + | + | − | − | + | 1 |
| PTCL51 | − | + | − | + | + | − | − | + | 0 |
| PTCL69 | + | + | ND | ND | + | − | − | + | 1 |
| PTCL71 | + | + | ND | ND | + | − | − | + | 1 |
| PTCL102 | − | + | + | + | + | − | − | + | 1 |
| PTCL105 | − | + | ND | + | + | − | − | + | 0 |
| PTCL117 | − | + | − | + | + | + | − | + | 1 |
| PTCL118 | + | ND | + | + | + | − | + | + | 1 |
| PTCL119 | − | − | + | + | + | − | − | + | 1 |
| PTCL124 | − | + | ND | ND | + | − | − | + | 0 |
| PTCL127 | + | + | ND | ND | + | − | − | + | 1 |
| PTCL128 | − | + | ND | ND | + | − | − | + | 0 |
| PTCL130 | + | − | ND | ND | + | − | − | + | 0 |
| PTCL132 | − | + | ND | ND | + | − | − | + | 0 |
| PTCL133 | − | + | ND | ND | + | − | − | + | 1 |
| PTCL147 | − | + | ND | ND | + | + | − | + | 0 |
| PTCL152 | − | + | ND | ND | + | − | − | + | 0 |
| PTCL154 | − | + | ND | ND | + | − | − | + | 0 |
| PTCL155 | − | + | ND | ND | + | − | − | + | 0 |
| PTCL5 | − | − | − | + | − | − | + | − | 0 |
| PTCL10 | − | − | − | + | + | + | + | − | 0 |
| PTCL12 | − | − | − | − | − | + | + | − | 0 |
| PTCL39 | − | ND | ND | + | + | − | − | − | 0 |
| PTCL43 | − | ND | ND | ND | + | + | ND | − | 0 |
| PTCL45 | − | − | − | + | + | − | − | − | 0 |
| PTCL47 | − | ND | − | − | + | − | − | − | 0 |
| PTCL52 | − | − | − | + | + | − | − | − | 0 |
| PTCL53 | − | − | − | + | + | − | − | − | 0 |
| PTCL58 | − | − | − | − | + | − | + | − | 0 |
| PTCL76 | − | + | ND | ND | − | − | − | − | 1 |
| PTCL87 | − | − | − | − | − | + | + | − | 0 |
| PTCL88 | − | ND | ND | − | + | − | − | − | 0 |
| PTCL95 | − | − | − | − | − | − | − | − | 0 |
| PTCL96 | − | − | − | − | − | − | + | − | 0 |
| PTCL97 | − | − | − | − | − | + | + | − | 0 |
| PTCL101 | − | − | − | ND | − | − | − | − | 0 |
| PTCL104 | − | ND | − | − | + | − | ND | − | 0 |
| PTCL110 | − | + | − | + | − | + | + | − | 0 |
| PTCL111 | − | − | ND | − | + | − | − | − | 0 |
| PTCL120 | − | − | − | + | − | + | + | − | 0 |
| PTCL122 | − | + | ND | ND | − | + | + | − | 1 |
| PTCL125 | − | − | ND | ND | − | + | + | − | 0 |
| PTCL129 | − | − | ND | ND | − | + | + | − | 0 |
| PTCL134 | − | − | ND | ND | + | − | − | − | 0 |
| PTCL139 | − | − | ND | ND | − | + | + | − | 0 |
| PTCL141 | − | − | ND | ND | − | + | + | − | 0 |
| PTCL143 | − | − | ND | ND | − | − | + | − | 0 |
| PTCL146 | − | − | ND | ND | + | − | − | − | 0 |
| PTCL149 | − | − | ND | ND | − | + | + | − | 0 |
| PTCL150 | − | − | ND | ND | − | + | + | − | 0 |
| PTCL151 | − | − | ND | ND | − | − | − | − | 0 |
| PTCL156 | − | − | ND | ND | + | − | − | − | 0 |
| PTCL158 | − | − | ND | ND | − | + | + | − | 0 |

Table 5 shows results of immunostaining for 59 PTCL-NOS cases, where they were determined to be a TFH case when CD4 and any one of supposedly AITL markers CD10, CD21 and PD-1 were stained, and also showing relationship with RHOA gene mutation.

(v) RHOA G17V is Molecule that is Deficient in GTP-Binding Ability (FIGS. 4, 5, 6 and 7)

RHOA is one of the well-studied low-molecular-weight GTPases. RHOA is known to play an important role in different kinds of biological events, and is known to be involved in cell skeleton, adhesion, motion and transcriptional activation of various cells including T cells. RHOA molecularly switches from a GTP-binding form (active form) to a GDP-binding form, and further to a GTP-binding form. Activation of RHOA involves GEF specific to the respective RHO molecules, where GEF catalyzes enzymatic conversion from GDP to GTP. The signal terminates upon conversion from GTP to GDP, where GAP is involved in this reaction. With respect to RHOA, although mutant RHOA G17A in which G17 has been artificially converted into alanine has been intensively studied until now, this mutant itself has not been found in cancer. Since RHOA G17A stably binds to GEF and does not bind to either GTP or GDP, it is considered to have lost a function as a molecular switch. There is no room for a water molecule to enter G17V due to the side chain of valine, where the GDP/GTP-binding pocket structure is disrupted and become unable to bind (FIG. 4).

Figure 4:
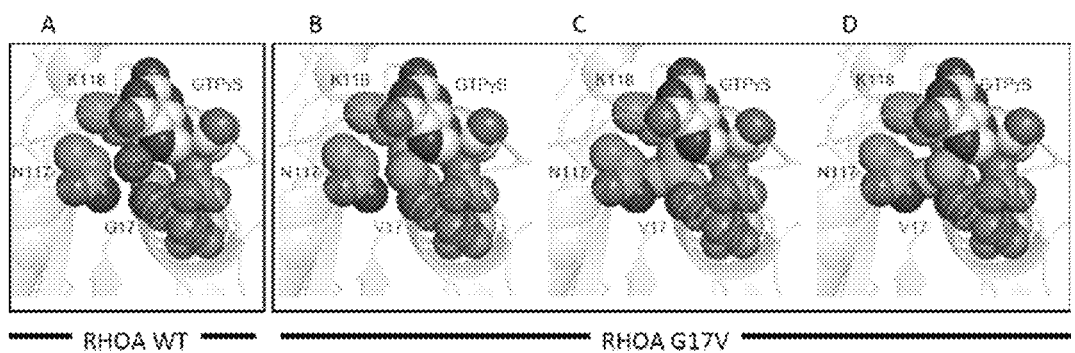
FIG. 4 Views showing three-dimensional structures of wild-type and mutant proteins of RHOA.

FIG. 4 shows views of three-dimensional structures of wild-type and G17V mutant RHOA proteins.

Figure 6:
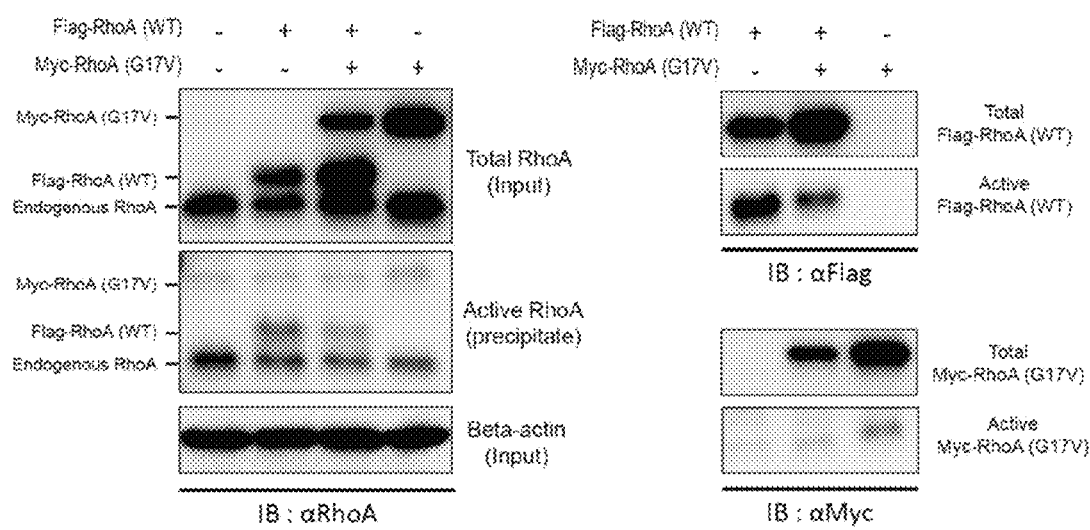
FIG. 6 Views showing results of an analysis of activities of the wild-type and mutant RHOA by pull-down assay.
Figure 7:
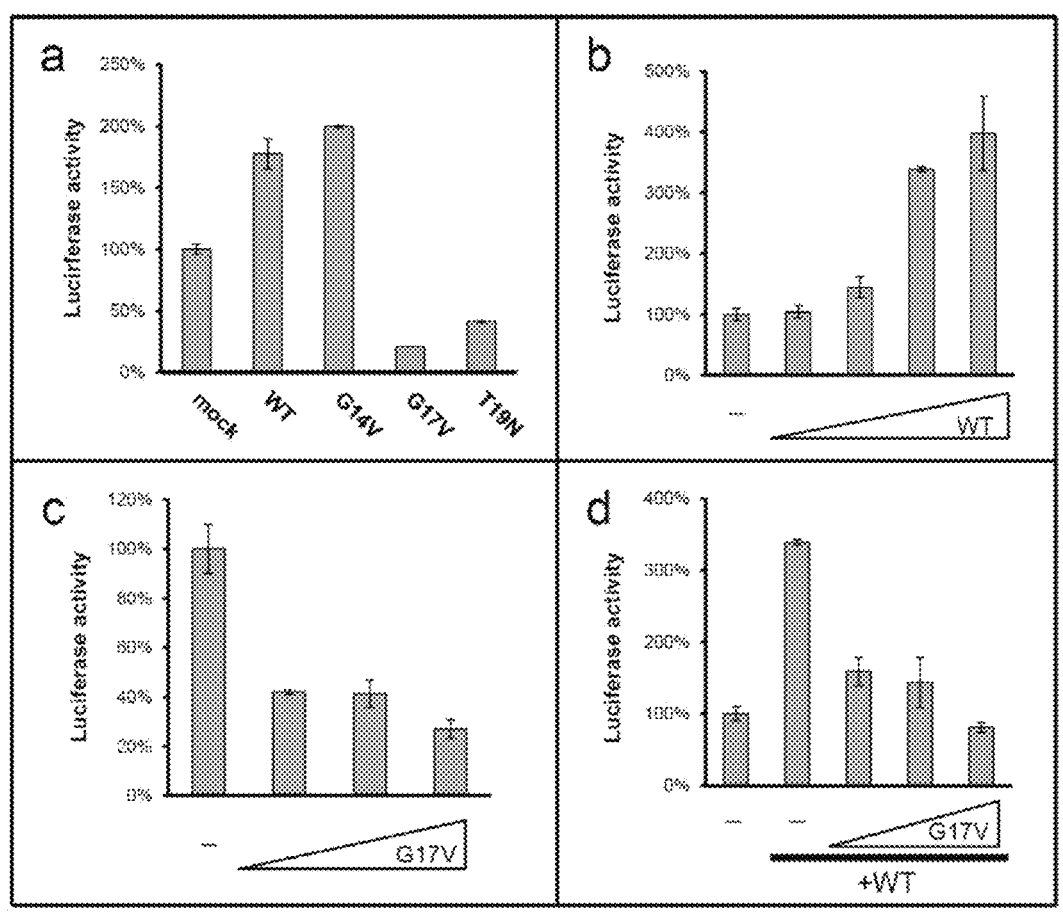
FIG. 7 Views showing results of an analysis of activities of the wild-type and mutant RHOA by reporter assay.

In order to examine the GTPase function of G17V, RHOA G17V cDNA was transfected into NIH-3T3, and the amount of RHOA protein that bound to Rhotekin that is known to specifically bind to GTP-binding-type Rho was determined, thereby determining the amount of the GTP-binding form. G17V had a smaller amount of GTP-binding form than the wild type (FIG. 5), and cotransfection of the wild type and G17V resulted a decrease in the amount of the GTP-binding wild type (FIG. 6). Additionally, RHOA activity was determined by SRE reporter assay. Endogenous RHOA activity or wild-type RHOA activity decreased by introducing G17V mutation (FIG. 7). These results show that the function of RHOA as a molecular switch decreased due to G17V mutation and that G17V suppresses a wild type in a dominant negative manner.

Figure 5:
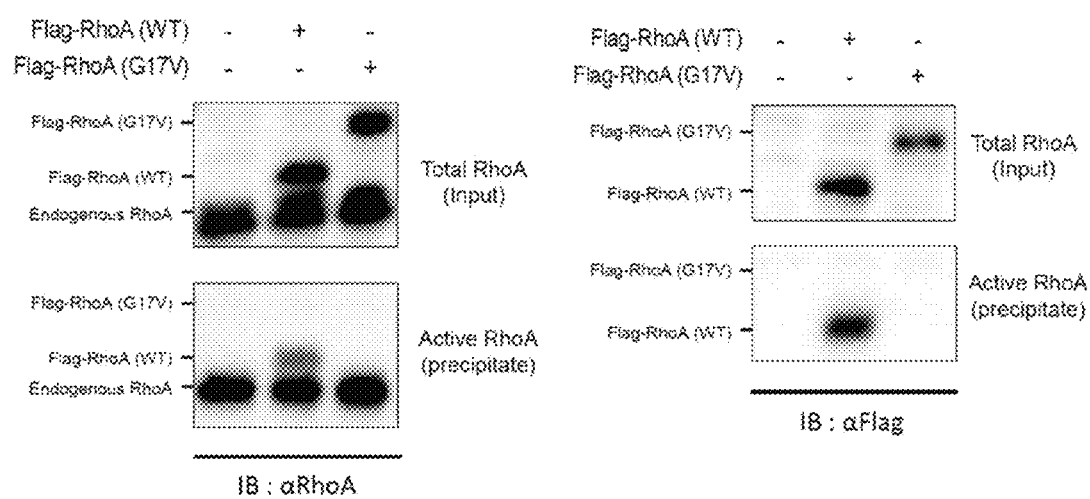
FIG. 5 Views showing results of an analysis of activities of the wild-type and mutant RHOA by pull-down assay.

FIG. 5 shows views of results of pull-down assay. Wild-type or G17V mutant RHOA was overexpressed in NIH-3T3 and the amount of GTP-gamma S-bound RHOA that binds to Rhotekin was quantitated to analyze the effect of RHOA G17V mutation on conversion into a GTP binding form.

FIGS. 6 and 7 show views of results from analyzing activities of wild-type and mutant RHOA. In FIG. 6, wild-type and G17V mutant RHOA were overexpressed in NIH-3T3 cells as the same time and the amount of GTP-binding wild-type RHOA that bound to Rhotekin was quantitated to analyze the effect of RHOA G17V mutation on conversion of wild-type RHOA into a GTP-binding form. In FIG. 7, as effects of RHOA G17V mutation on the serum responsive factor response element (SRE), (a) SRE activity upon introducing wild-type and mutant (G14V, G17V, T19N) RHOA into NIH-3T3, (b) SRE activity upon introducing wild-type RHOA, (c) an effect on SRE activity of endogenous RhoA upon introducing RhoA G17V, and (d) an effect on SRE activity upon introducing RhoA G17V and a wild type at the same time, were analyzed.

Figure 8:
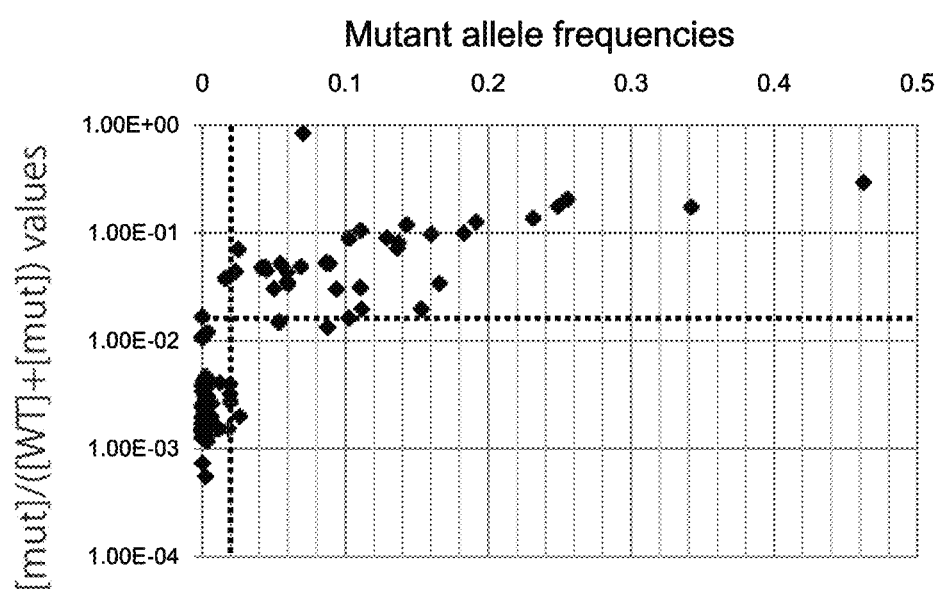
FIG. 8 A diagram showing results of an analysis of mutant allele frequencies by deep sequencing method.

(vi) Relationship Between Mutant Allele Frequencies (Deep Sequencing) and Amounts of Mutant Alleles ([mut]/([mut]+[WT])) (FIG. 8)

FIG. 8 is a diagram showing results from an analysis of mutant allele frequencies by deep sequencing method.

Calculation of [mut]/([mut]+[WT]) value resulted dispersed values of $5.6 \times 10^{-4}$ to $8.5 \times 10^{-1}$. Frequencies of mutant alleles determined with [mut]/([mut]+[WT]) values and MiSeq indicated a positive correlation (rank-correlation coefficient r=0.785, p<0.01). By setting the cutoff level for [mut]/([mut]+[WT]) to 0.015 and the mutant allele frequencies to 2%, the detection sensitivity and specificity became 94.7% and 96.5%, respectively.

From the above results, a method for detecting RHOA gene mutation for AITL diagnosis was established. This method is expected to realize high accuracy and cost effectiveness.

(vii) Detection of RHOA Mutation in Serum

For six T-cell lymphoma patients having RHOA mutation in the tumors, DNA was extracted from sera using DNA blood mini kit (QIAGEN). After preparing PCR amplicons, mutant allele frequencies were analyzed by deep sequencing method on PGM.

As a result, mutant alleles were also detected in sera for 5 out of 6 cases at a cutoff of 0.2%. On the other hand, no mutant allele was detected in the sera for 4 cases where tumors did not contain RHOA mutation.

TABLE 6

| Patients | Mutant allele frequencies in tumor (%) | Mutant allele frequencies in serum (%) |
|---|---|---|
| 1 | 6.9 | 1.46 |
| 2 | 6.7 | 0.57 |
| 3 | 8.5 | 0.44 |
| 4 | 5.5 | 1.37 |
| 5 | 14.8 | 6.61 |
| 6 | 35.6 | 0.08 |

Sequence Listing: Free Text

SEQ ID NO:3: A sequence of three nucleotides may be deleted (existing positions: 49-51).

Sequence Listing

The invention claimed is:

1. A method for treating peripheral T-cell lymphoma in a human subject comprising the steps of:
   analyzing position 50 of SEQ ID NO: 1 in a ras homolog family member A (RHOA) gene collected from a sample of the subject;
   providing one or more oligonucleotide probes, wherein the oligonucleotide probes comprises position 50 of SED ID NO: 1 and comprises at least 10 to 50 nucleotides in length of SEQ ID NO:1;
   detecting by hybridization the presence of a T at position 50 of SEQ ID NO: 1,
   determining the subject who has a T at position 50 of SEQ ID NO: 1 has or is at risk of developing angioimmunoblastic T-cell lymphoma (AITL) or a peripheral T-cell lymphoma not otherwise specified (PTCL-NOS); and
   administering a therapeutic agent for the peripheral T-cell lymphoma to the subject who has or has been determined to have the risk of AITL or PTCL-NOS.

* * * * *

SEQUENCE LISTING

<160> NUMBER OF SEQ ID NOS: 3

<210> SEQ ID NO 1
<211> LENGTH: 582
<212> TYPE: DNA
<213> ORGANISM: Homo sapiens
<220> FEATURE:
<221> NAME/KEY: CDS
<222> LOCATION: (1)..(579)

<400> SEQUENCE: 1

```
atg gct gcc atc cgg aag aaa ctg gtg att gtt ggt gat gga gcc tgt      48
Met Ala Ala Ile Arg Lys Lys Leu Val Ile Val Gly Asp Gly Ala Cys
1               5                   10                  15 gga aag aca tgc ttg ctc ata gtc ttc agc aag gac cag ttc cca gag      96
Gly Lys Thr Cys Leu Leu Ile Val Phe Ser Lys Asp Gln Phe Pro Glu
            20                  25                  30 gtg tat gtg ccc aca gtg ttt gag aac tat gtg gca gat atc gag gtg    144
Val Tyr Val Pro Thr Val Phe Glu Asn Tyr Val Ala Asp Ile Glu Val
        35                  40                  45 gat gga aag cag gta gag ttg gct ttg tgg gac aca gct ggg cag gaa    192
Asp Gly Lys Gln Val Glu Leu Ala Leu Trp Asp Thr Ala Gly Gln Glu
    50                  55                  60 gat tat gat cgc ctg agg ccc ctc tcc tac cca gat acc gat gtt ata    240
Asp Tyr Asp Arg Leu Arg Pro Leu Ser Tyr Pro Asp Thr Asp Val Ile
65                  70                  75                  80 ctg atg tgt ttt tcc atc gac agc cct gat agt tta gaa aac atc cca    288
Leu Met Cys Phe Ser Ile Asp Ser Pro Asp Ser Leu Glu Asn Ile Pro
                85                  90                  95 gaa aag tgg acc cca gaa gtc aag cat ttc tgt ccc aac gtg ccc atc    336
Glu Lys Trp Thr Pro Glu Val Lys His Phe Cys Pro Asn Val Pro Ile
            100                 105                 110 atc ctg gtt ggg aat aag aag gat ctt cgg aat gat gag cac aca agg    384
Ile Leu Val Gly Asn Lys Lys Asp Leu Arg Asn Asp Glu His Thr Arg
        115                 120                 125 cgg gag cta gcc aag atg aag cag gag ccg gtg aaa cct gaa gaa ggc    432
Arg Glu Leu Ala Lys Met Lys Gln Glu Pro Val Lys Pro Glu Glu Gly
    130                 135                 140 aga gat atg gca aac agg att ggc gct ttt ggg tac atg gag tgt tca    480
Arg Asp Met Ala Asn Arg Ile Gly Ala Phe Gly Tyr Met Glu Cys Ser
145                 150                 155                 160 gca aag acc aaa gat gga gtg aga gag gtt ttt gaa atg gct acg aga    528
Ala Lys Thr Lys Asp Gly Val Arg Glu Val Phe Glu Met Ala Thr Arg
                165                 170                 175 gct gct ctg caa gct aga cgt ggg aag aaa aaa tct ggg tgc ctt gtc    576
Ala Ala Leu Gln Ala Arg Arg Gly Lys Lys Lys Ser Gly Cys Leu Val
            180                 185                 190 ttg tga                                                             582
Leu
```

<210> SEQ ID NO 2
<211> LENGTH: 193
<212> TYPE: PRT
<213> ORGANISM: Homo sapiens

<400> SEQUENCE: 2

```
Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95
```

```
Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
            180                 185                 190

Leu

<210> SEQ ID NO 3
<211> LENGTH: 582
<212> TYPE: DNA
<213> ORGANISM: Homo sapiens
<220> FEATURE:
<221> NAME/KEY: misc_structure
<222> LOCATION: (49)..(51)
<223> OTHER INFORMATION: A sequence gga may be deleted
<220> FEATURE:
<221> NAME/KEY: misc_structure
<222> LOCATION: (49)..(51)
<223> OTHER INFORMATION: Three base sequences may be deleted

<400> SEQUENCE: 3
atggctgcca tccggaagaa actggtgatt gttggtgatg gagcctgtgk aaagacatgc    60
ttgctcatag tcttcagcaa ggaccagttc ccagaggtgt atgtgcccac agtgtttgag   120
aactatgtgg cagatatcga ggtggatgga aagcaggtag agttggcttt gtgggacaca   180
gctgggcagg aagattatga tcgcctgagg cccctctcct acccagatac cgatgttata   240
ctgatgtgtt tttccatcga cagccctgat agtttagaaa acatcccaga aaagtggacc   300
ccagaagtca agcatttctg tcccaacgtg yccrtcatcc tggttgggaa taagaaggat   360
cttcggaatg atgagcacac aaggcgggag ctagccaaga tgaagcagga gccggtgaaa   420
cctgaagaag gcagagatat ggcaaacagg attggcgctt ttgggtacat ggagtgttca   480
gmaaagacca aagatggagt gagagaggtt tttgaaatgg ctacgagagc tgctctgcaa   540
gctagacgtg ggaagaaaaa atctgggtgc cttgtcttgt ga                      582
```